(12) United States Patent
Dollinger et al.

(10) Patent No.: US 7,648,988 B2
(45) Date of Patent: Jan. 19, 2010

(54) SUBSTITUTED PTERIDINES FOR THE TREATMENT OF INFLAMMATORY DISEASES

(75) Inventors: Horst Dollinger, Schemmerhofen (DE); Domnic Martyres, Biberach (DE); Juergen Mack, Biberach (DE); Peter Nickolaus, Warthausen (DE); Birgit Jung, Laupheim (DE)

(73) Assignee: Boehringer Ingelheim International GmbH, Ingelheim am Rhein ( * ) Notice: Subject to any disclaimer, the term of this patent is extended or adjusted under 35 U.S.C. 154(b) by 0 days.

(21) Appl. No.: 12/031,396

(22) Filed: Feb. 14, 2008

(65) Prior Publication Data

US 2008/0153833 A1 Jun. 26, 2008

Related U.S. Application Data

(63) Continuation of application No. 11/282,125, filed on Nov. 18, 2005, now abandoned.

(30) Foreign Application Priority Data

Nov. 29, 2004 (DE) .................. 10 2004 057 594

(51) Int. Cl.
 C07D 475/08 (2006.01)
 A61K 31/4985 (2006.01)
 A61K 31/541 (2006.01)
 A61K 31/5355 (2006.01)
 A61P 1/00 (2006.01)
 A61P 11/00 (2006.01)
 A61P 35/00 (2006.01)
 A61P 29/00 (2006.01)
 A61P 25/00 (2006.01)
 A61P 25/02 (2006.01)

(52) U.S. Cl. .................. 514/249; 544/260; 544/58.2; 544/61

(58) Field of Classification Search .................. 514/249, 514/211.15, 228.5, 234.2; 544/260, 58.2, 544/118; 540/544
See application file for complete search history.

(56) References Cited

U.S. PATENT DOCUMENTS

| 2,940,972 | A | 6/1960 | Roch |
| 4,560,685 | A | 12/1985 | Roch et al. |
| 7,205,408 | B2 | 4/2007 | Davies |
| 2005/0054653 | A1 | 3/2005 | Eisenbrand et al. |
| 2006/0116371 | A1 | 6/2006 | Martyres et al. |
| 2006/0116372 | A1 | 6/2006 | Dollinger et al. |
| 2006/0116373 | A1 | 6/2006 | Dollinger et al. |

FOREIGN PATENT DOCUMENTS

| CA | 1233179 | 2/1988 |
| CA | 1252783 | 4/1989 |
| CA | 1337813 | 12/1995 |
| DE | 3323932 A1 | 1/1985 |
| DE | 3445298 A1 | 6/1986 |
| DE | 3540952 | 5/1987 |
| EP | 0134922 A | 3/1985 |
| EP | 0185259 | 5/1987 |
| GB | 2143232 | 2/1985 |
| WO | 0039129 A1 | 7/2000 |
| WO | 03062240 | 7/2003 |
| WO | 03062240 A1 | 7/2003 |

OTHER PUBLICATIONS

Marko, et al., Biochem. Pharmacol. (2002), 63(4), 669-676.*
Yamamoto, K. et al.; Differential activity of drugs to induce emesis and pica behavior in *Suncus murinus* (house musk shrew) and rats, Physiology & Behavior; 2004; vol. 83; pp. 151-156.
Merz, et al; Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth; Journal of Medicinal Chemistry, American Chemical Society; 1998; vol. 41(24); pp. 4733-4743.
Doherty; Phosphodiesterase 4 inhibitors as novel anti-inflammatory agents; Current Opinion in Chemical Biology; 1999; No. 3; pp. 466-473.

* cited by examiner

*Primary Examiner*—Mark L Berch
*Assistant Examiner*—Cecilia M Jaisle
(74) *Attorney, Agent, or Firm*—Michael P. Morris; Mary-Ellen M. Devlin; Alan R. Stempel

(57) ABSTRACT

Described are new pteridine compounds of the formula 1,

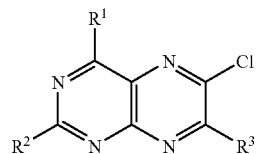

where the variables are as described herein. The compounds are useful for the treatment of: respiratory or gastrointestinal complaints or diseases; inflammatory diseases of the joints, skin or eyes; diseases of the peripheral or central nervous system; and cancers. Also described are pharmaceutical compositions which contain these compounds.

6 Claims, No Drawings

SUBSTITUTED PTERIDINES FOR THE TREATMENT OF INFLAMMATORY DISEASES

CROSS-REFERENCE TO RELATED APPLICATIONS

This application is a continuation of U.S. patent application Ser. No. 11/282,125, filed Nov. 18, 2005, the entirety of which is incorporated herein by reference.

The invention relates to new pteridines which are suitable for the treatment of respiratory or gastrointestinal complaints or diseases, inflammatory diseases of the joints, skin or eyes, diseases of the peripheral or central nervous system or cancers, as well as pharmaceutical compositions which contain these compounds.

PRIOR ART

Pteridines are known from the prior art as active substances with an antiproliferative activity. Merz et al. describe in the Journal of Medicinal Chemistry 1998, 41, 4733-4743 the preparation of 7-benzylamino-6-chloro-2-piperazino-4-pyrrolidinopteridine and derivatives thereof which are free from positional isomers. It has been shown that the compounds prepared are able to inhibit the growth of tumour cells. DE 3540952 describes 2-piperazino-pteridines which are substituted in the 6 position by a halogen atom, selected from among fluorine, chlorine or bromine. It has been shown that these compounds were able to inhibit the activity of tumour cells and human thrombocytes in vitro. DE 3323932 discloses 2-piperazino-pteridines which carry a dialkylamino, piperidino, morpholino, thiomorpholino or 1-oxidothiomorpholino group in the 4 position. It has been shown that these compounds were able to inhibit the activity of tumour cells and human thrombocytes in vitro. DE 3445298 describes pteridines with a large number of different substituents in the 2, 4, 6 and 7 position, while compounds with a 2-piperazino group on the pteridine skeleton are suitable as inhibitors of tumour growth as well as having antithrombotic and metastasis-inhibiting properties. U.S. Pat. No. 2,940,972 discloses tri- and tetrasubstituted pteridine derivatives, while general statements are made to the effect that these pteridines have valuable pharmacological properties, namely coronary-dilatory, sedative, antipyretic and analgesic effects.

The phosphodiesterase 4 inhibitors known from the prior art are known to trigger side effects such as nausea and vomiting (Doherty, 1999, Curr. Op. Chem. Biol., August 3, (4): 466-73). The substances mentioned in this invention are particularly preferably suitable for the treatment of the above-mentioned diseases, as they did not cause these side effects in an animal model for nausea and vomiting (S. Murinus, Yamamoto K. et al., Physiol. Behav., 2004, Oct. 30, 83(1), 151-6).

The aim of the present invention is to provide new compounds which are suitable for the prevention or treatment of respiratory or gastrointestinal complaints or diseases, inflammatory diseases of the joints, skin or eyes, diseases of the peripheral or central nervous system, or cancers, particularly those compounds which are characterised by reduced side effects, particularly emesis and nausea.

DESCRIPTION OF THE INVENTION

Surprisingly it has now been found that pteridines of formula 1 are suitable for the treatment of inflammatory diseases. The present invention therefore relates to compounds of formula 1

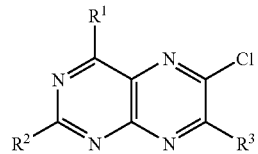

wherein $R^1$ denotes a saturated or unsaturated, five-, six- or seven-membered, heterocyclic ring which may contain a nitrogen atom and another atom selected from among nitrogen, sulphur and oxygen;

$R^2$ denotes a five-, six- or seven-membered heterocyclic ring which may contain a nitrogen atom and another atom selected from among nitrogen, sulphur and oxygen;

$R^3$ denotes a group of formula 1a,

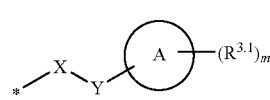

wherein

A denotes aryl;

X denotes $NR^{3.2}$, S, O;

Y denotes $C_{1-4}$-alkylene, substituted by one or more $R^{3.3}$ m denotes 0, 1, 2;

$R^{3.1}$ each independently of one another denote $C_{1-4}$-alkyl, aryl, $COOR^{3.1.1}$, $CONR^{3.1.1}R^{3.1.2}$, CN, $NR^{3.1.1}R^{3.1.2}$, $NHCOR^{3.1.1}$, $OR^{3.1.1}$, $O-C_{1-4}$-haloalkyl, $SO_2R^{3.1.1}$, $SO_2NH_2$, halogen, $C_{1-6}$-haloalkyl, $C_{1-6}$-alkyl-$CONH_2$, $O-C_{1-6}$-alkyl-$NH_2$, $O-C_{3-6}$-cycloalkyl, $O-C_{1-4}$-alkylene-$C_{3-6}$-cycloalkyl;

$R^{3.1.1}$ denotes H, $C_{1-4}$-alkyl;

$R^{3.1.2}$ denotes H, $C_{1-4}$-alkyl; or $R^{3.1}$ together with two atoms of A forms a 5- or 6-membered carbocyclic ring or a 5- or 6-membered heterocyclic ring which may contain one or more oxygen or nitrogen atoms;

$R^{3.2}$ denotes H, $C_{1-6}$-alkyl;

$R^{3.3}$ each independently of one another denote $C_{1-6}$-alkyl, $C_{1-6}$-alkyl-OH, $C_{3-6}$-cycloalkyl, $C_{3-6}$-cycloalkyl-OH, $O-C_{1-6}$-alkyl, COOH, COO-$C_{1-6}$-alkyl, $CONH_2$;

$R^{3.3}$ together with one or two carbon atoms of Y forms a carbocyclic ring with 3, 4, 5 or 6 carbon atoms and pharmacologically acceptable salt, diastereomers, enantiomers, racemates, hydrates or solvates thereof.

Preferred compounds of formula 1 above are those wherein $R^1$ denotes a saturated or unsaturated, five- or six-membered heterocyclic ring which may contain a nitrogen atom and another atom selected from among nitrogen and sulphur;

$R^2$ denotes a five- or six-membered heterocyclic ring which may contain one or two nitrogen atoms;

and pharmacologically acceptable salt, diastereomers, enantiomers, racemates, hydrates or solvates thereof.

Preferred compounds of formula 1 above are those wherein
$R^1$ denotes a saturated or unsaturated, five- or six-membered heterocyclic ring which may contain a nitrogen atom and optionally contains a further sulphur atom;
$R^2$ denotes a six-membered heterocyclic ring which contains two nitrogen atoms;

and pharmacologically acceptable salt, diastereomers, enantiomers, racemates, hydrates or solvates thereof.

Preferred compounds of formula 1 above are those wherein
$R^3$ denotes a group of formula 1a,
wherein
A denotes aryl;
X denotes $NR^{3.2}$, S, O;
Y denotes $C_{1-4}$-alkylene, substituted by one or more $R^{3.3}$
m denotes 0, 1, 2;
$R^{3.1}$ each independently of one another denote $C_{1-4}$-alkyl, aryl, $COOR^{3.1.1}$, $CONR^{3.1.1}R^{3.1.2}$, CN, $NR^{3.1.1}R^{3.1.2}$, $NHCOR^{3.1.1}$, $OR^{3.1.1}$, O—$C_{1-4}$-haloalkyl, $SO_2R^{3.1.1}$, $SO_2NH_2$, halogen, $C_{1-6}$-haloalkyl, $C_{1-6}$-alkyl-$CONH_2$, O—$C_{1-6}$-alkyl-$NH_2$, O—$C_{3-6}$-cycloalkyl, O—$C_{1-4}$-alkylene-$C_{3-6}$-cycloalkyl;
$R^{3.1.1}$ denotes H, $C_{1-4}$-alkyl;
$R^{3.1.2}$ denotes H, $C_{1-4}$-alkyl;
$R^{3.2}$ denotes H, $C_{1-6}$-alkyl;
$R^{3.3}$ each independently of one another denote $C_{1-6}$-alkyl, $C_{1-6}$-alkyl-OH, $C_{3-6}$-cycloalkyl, $C_{3-6}$-cycloalkyl-OH, O—$C_{1-6}$-alkyl, COOH, COO—$C_{1-6}$-alkyl, $CONH_2$;
$R^{3.3}$ together with one or two carbon atoms of Y forms a carbocyclic ring with 3, 4, 5 or 6 carbon atoms and the pharmacologically acceptable salt, diastereomers, enantiomers, racemates, hydrates or solvates thereof.

Preferred compounds of formula 1 are those wherein
$R^3$ is a group of general formula 1a, wherein
A denotes phenyl;
X denotes $NR^{3.2}$, S, O;
Y denotes $C_{1-4}$-alkylene, substituted by one or more $R^{3.3}$
m denotes 0, 1 or 2;
$R^{3.1}$ each independently of one another denote $C_{1-4}$-alkyl, aryl, $COOR^{3.1.1}$, $CONR^{3.1.1}R^{3.1.2}$, CN, $NR^{3.1.1}R^{3.1.2}$, $NHCOR^{3.1.1}$, $OR^{3.1.1}$, O—$C_{1-4}$-haloalkyl, $SO_2R^{3.1.1}$, $SO_2NH_2$, halogen;
$R^{3.1.1}$ denotes H, $C_{1-6}$-alkyl;
$R^{3.1.2}$ denotes H, $C_{1-6}$-alkyl;
$R^{3.2}$ denotes H, $C_{1-6}$-alkyl;
$R^{3.3}$ each independently of one another denote $C_{1-6}$-alkyl, $C_{1-6}$-alkyl-OH, $C_{3-6}$-cycloalkyl, O—$C_{1-6}$-alkyl, COOH, COO—$C_{1-6}$-alkyl, $CONH_2$;
$R^{3.3}$ together with one or two carbon atoms of Y forms a carbocyclic ring with 3, 5 or 6 carbon atoms and the pharmacologically acceptable salt, diastereomers, enantiomers, racemates, hydrates or solvates thereof.

Preferred compounds of formula 1 above are those wherein
$R^3$ is a group of general formula 1a, wherein
A denotes phenyl;
X denotes $NR^{3.2}$;
Y denotes $C_{1-2}$-alkylene, substituted by one or more $R^{3.3}$
m denotes 0, 1 or 2;
$R^{3.1}$ each independently of one another denote $C_{1-4}$-alkyl, aryl, $COOR^{3.1.1}$, $CONR^{3.1.1}R^{3.1.2}$, CN, $NR^{3.1.1}R^{3.1.2}$, $NHCOR^{3.1.1}$, $OR^{3.1.1}$, O—$C_{1-4}$-haloalkyl, $SO_2R^{3.1.1}$, $SO_2NH_2$, halogen;
$R^{3.1.1}$ denotes H, $C_{1-4}$-alkyl;
$R^{3.1.2}$ denotes H, $C_{1-4}$-alkyl;
$R^{3.2}$ denotes H, $C_{1-4}$-alkyl;
$R^{3.3}$ each independently of one another denote $C_{1-4}$-alkyl, $C_{1-4}$-alkyl-OH, $C_{3-6}$-cycloalkyl, O—$C_{1-4}$-alkyl, COOH, COO—$C_{1-4}$-alkyl, $CONH_2$;
$R^{3.3}$ together with one or two carbon atoms of Y forms a carbocyclic ring with 3, 5 or 6 carbon atoms and the pharmacologically acceptable salt, diastereomers, enantiomers, racemates, hydrates or solvates thereof.

Preferred compounds of formula 1 above are those wherein
$R^3$ is a group of general formula 1a, wherein
A denotes phenyl;
X denotes $NR^{3.2}$;
Y denotes $C_{1-2}$-alkylene, substituted by one or more $R^{3.3}$
m denotes 0, 1 or 2;
$R^{3.1}$ each independently of one another denote $C_{1-4}$-alkyl, aryl, COOH, COO—$C_{1-4}$-alkyl, $CONH_2$, CN, $NH_2$, NHCO—$C_{1-4}$-alkyl, OH, O—$C_{1-4}$-alkyl, O—$C_{1-4}$-haloalkyl, $SO_2$—$C_{1-4}$-alkyl, $SO_2NH_2$, halogen;
$R^{3.2}$ denotes H, $C_{1-4}$-alkyl;
$R^{3.3}$ each independently of one another denote $C_{1-4}$-alkyl, $C_{1-4}$-alkyl-OH, $C_{3-6}$-cycloalkyl, O—$C_{1-4}$-alkyl, COOH, COO—$C_{1-4}$-alkyl, $CONH_2$;
$R^{3.3}$ together with one or two carbon atoms of Y forms a carbocyclic ring with 3, 5 or 6 carbon atoms and the pharmacologically acceptable salt, diastereomers, enantiomers, racemates, hydrates or solvates thereof.

Preferred compounds of formula 1 above are those wherein
$R^3$ is a group of general formula 1a, wherein
A denotes phenyl;
X denotes $NR^{3.2}$;
Y denotes $C_{1-2}$-alkylene, substituted by one or more $R^{3.3}$
m denotes 0, 1 or 2;
$R^{3.1}$ each independently of one another denote methyl, ethyl, propyl, Ph, COOH, COOMe, $CONH_2$, CN, $NH_2$, NHCOMe, OH, OMe, OEt, $OCF_3$, $OCHF_2$, $SO_2Me$, $SO_2NH_2$, F, Cl, Br;
$R^{3.2}$ denotes H, $C_{1-4}$-alkyl;
$R^{3.3}$ each independently of one another denote methyl, ethyl, propyl, butyl, $CH_2OH$, $CH_2CH_2OH$, $C(CH_2)_2OH$, cyclopropyl, COOH, COOMe, COOEt, COOPr, $CONH_2$, OMe, OEt, OPr;
$R^{3.3}$ together with one or two carbon atoms of Y forms a carbocyclic ring with 3, 5 or 6 carbon atoms and the pharmacologically acceptable salt, diastereomers, enantiomers, racemates, hydrates or solvates thereof.

Also preferred are the above compounds of formula 1, wherein
$R^3$ is a group of general formula 1a, wherein
A denotes phenyl;
X denotes $NR^{3.2}$;
Y denotes $C_{1-2}$-alkylene, substituted by one or more $R^{3.3}$
m denotes 0, 1 or 2;
$R^{3.1}$ each independently of one another denote $C_{1-4}$-alkyl, CN, O—$C_{1-4}$-alkyl, halogen;
$R^{3.2}$ denotes H;
$R^{3.3}$ each independently of one another denote $C_{1-4}$-alkyl, $C_{1-4}$-alkyl-OH, $C_{3-6}$-cycloalkyl, COOH, COO—$C_{1-4}$-alkyl, $CONH_2$, O—$C_{1-4}$-alkyl;
$R^{3.3}$ together with one or two carbon atoms of Y forms a carbocyclic ring with 3, 5 or 6 carbon atoms and the pharmacologically acceptable salt, diastereomers, enantiomers, racemates, hydrates or solvates thereof.

Preferred compounds of formula 1 above are those wherein $R^3$ is a group of general formula 1a, wherein
- A denotes phenyl;
- X denotes $NR^{3.2}$;
- Y denotes $C_{1-2}$-alkylene, substituted by one or more $R^{3.3}$
- m denotes 0, 1 or 2;
- $R^{3.1}$ each independently of one another denote methyl, iso-propyl, OMe, F, Cl, Br, CN,
- $R^{3.2}$ denotes H;
- $R^{3.3}$ each independently of one another denote methyl, cyclopropyl, $CH_2OH$, $CH_2CH_2OH$, $C(CH_2)_2OH$, COOH, COOMe, $CONH_2$, OMe,
- $R^{3.3}$ together with one or two carbon atoms of Y forms a carbocyclic ring with 3 carbon atoms and the pharmacologically acceptable salt, diastereomers, enantiomers, racemates, hydrates or solvates thereof.

Particularly preferred are the above compounds of formula 1, wherein
- $R^1$ denotes pyrrolidinyl, 2.5-dihydro-1H-pyrrolyl, thiomorpholinyl;
- $R^2$ denotes piperazinyl;
- $R^3$ a group selected from among

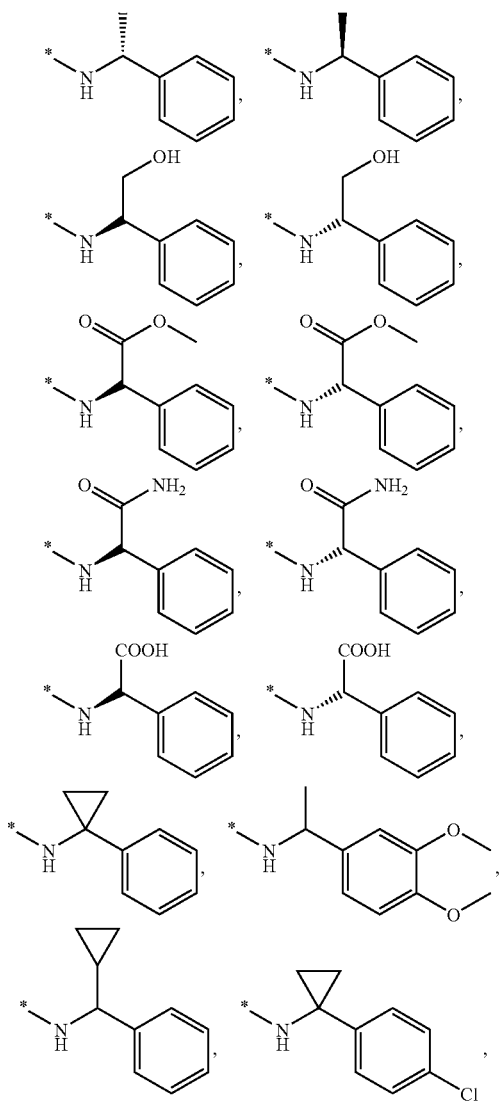

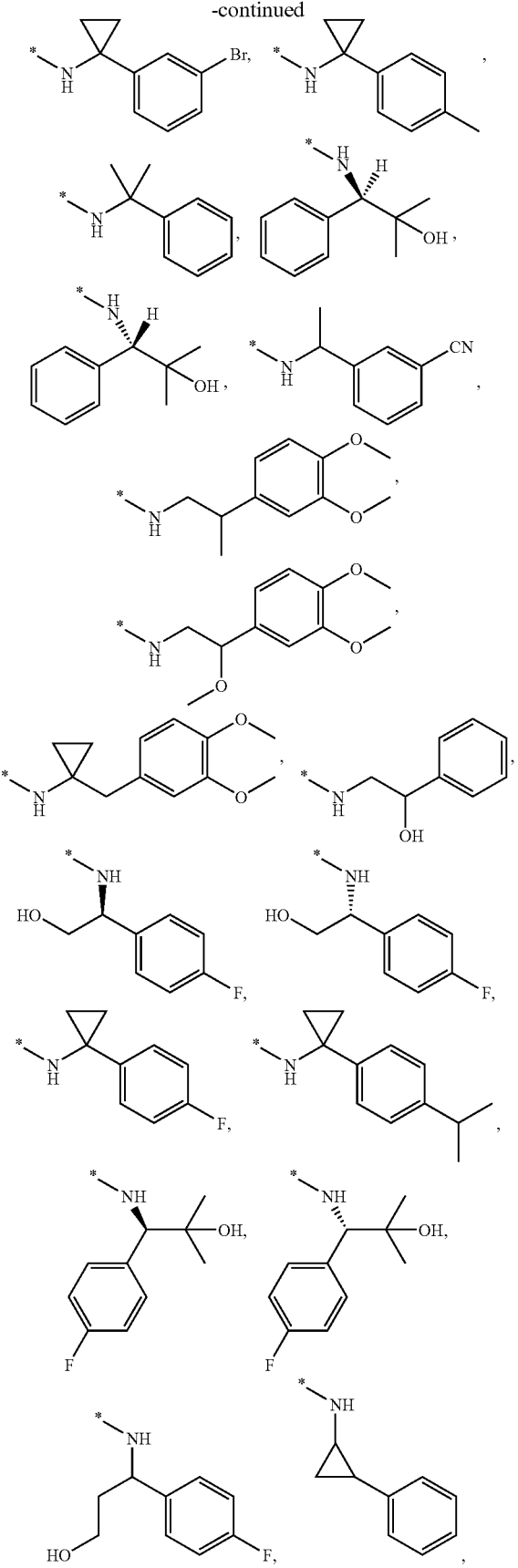

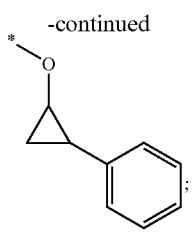

and pharmacologically acceptable salt, diastereomers, enantiomers, racemates, hydrates or solvates thereof.

Terms and Definitions Used

Within the scope of this application, when defining possible substituents, these may also be shown in the form of a structural formula. An asterisk (*) in the structural formula of the substituent is construed as the binding site to the rest of the molecule. Thus, for example, the groups N-piperidinyl (I), 4-piperidinyl (II), 2-tolyl (III), 3-tolyl (IV) and 4-tolyl (V) are shown as follows:

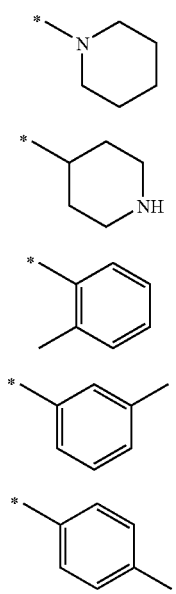

If there is no asterisk (*) in the structural formula of the substituent, each hydrogen atom may be removed from the substituent and the valency thus liberated may serve as a binding site to the rest of a molecule. Thus, for example, VI may represent 2-tolyl, 3-tolyl, 4-tolyl and benzyl.

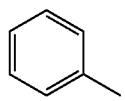

By pharmacologically acceptable acid addition salts are meant for example those salts which are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neo-pentyl or hexyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-4}$-alkylene" (including those which are part of other groups) are meant branched and unbranched alkylene groups with 1 to 4 carbon atoms. Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene. If the carbon chain is substituted by a group which forms together with one or two carbon atoms of the alkylene chain a carbocyclic ring with 3, 4, 5 or 6 carbon atoms, the following are thus included as examples of the rings:

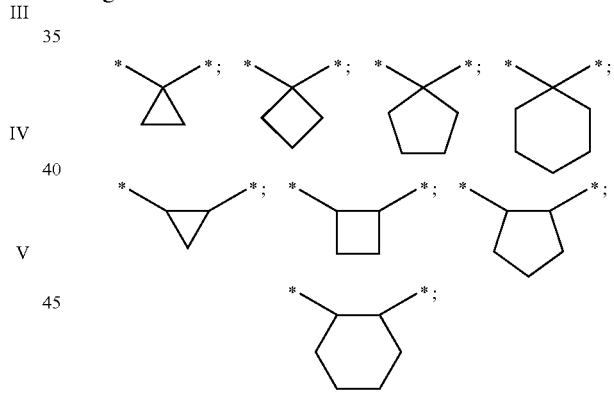

By the term "$C_{3-6}$-cycloalkyl" (including those which are part of other groups) are meant cyclic alkyl groups with 3 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

Halogen within the scope of the present invention denotes fluorine, chlorine, bromine or iodine. Unless stated to the contrary, fluorine, chlorine and bromine are regarded as preferred halogens.

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "heterocyclic rings" or "het" are meant five-, six- or seven-membered, saturated or unsaturated heterocyclic rings or 5-10 membered, bicyclic heterorings which may contain one, two or three heteroatoms, selected from among oxygen, sulphur and nitrogen, while the ring may be linked to the molecule through a carbon atom or, if available, through a nitrogen atom. The following are examples of five-, six- or seven-membered, saturated or unsaturated heterocyclic rings:

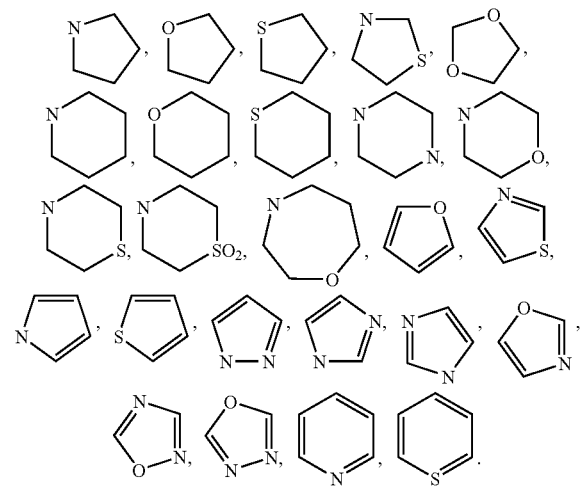

Unless otherwise mentioned, a heterocyclic ring may be provided with a keto group. Examples of this include:

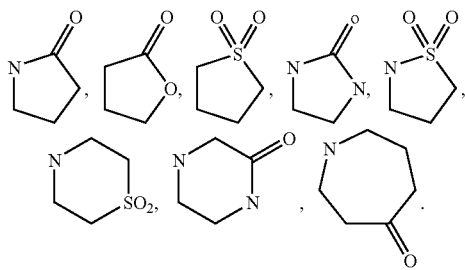

EXAMPLES

The compounds according to the invention may be prepared by methods known per se from the literature, as described for example in DE 3540952. Other alternative methods of preparing the compounds listed below are described hereinafter.

Compound 12: a) 1-phenyl-cyclopropanecarbonyl chloride: 7.00 g (41.87 mmol) 1-phenylcyclopropanecarboxylic acid, 30.45 ml (418.70 mmol) thionyl chloride and 1 drop of dimethylformamide are placed in 100 ml dichloromethane, then refluxed for 3 hours with stirring. Then the reaction mixture is concentrated by evaporation, taken up in toluene and evaporated down again. The residue is combined and extracted with water and dichloromethane. The organic phase is washed with water, dried and evaporated to dryness. Yield: 7.53 g b) 1-phenyl-cyclopropylamine: 7.53 g (41.69 mmol) 1-phenyl-cyclopropanecarbonyl chloride are placed in 50 ml xylene, 3.25 g (50.03 mmol) sodium azide are added. The reaction mixture is first heated to 80° C., after 1 hour heated to 110° C. and stirred for another 1 hour. After cooling to ambient temperature the mixture is filtered and conc. hydrochloric acid is added to the filtrate. It is heated to 70° C. until the development of $CO_2$, has ended, then stirred for 1 hour at 100° C. Then the reaction mixture is extracted with 4 N hydrochloric acid, the aqueous phase is made alkaline and extracted with petroleum ether. The organic phase is dried and evaporated to dryness.

Yield: 1.07 g (=19% of theoretical)

c) (6-chloro-2-piperazin-1-yl-4-pyrrolidin-1-yl-pteridin-7-yl)-(1-phenyl-cyclopropyl)-amine (Example 12): 80 mg (0.263 mmol) 2,6,7-trichloro-4-pyrrolidin-1-yl-pteridine are dissolved in 5 ml dioxane, and 0.064 ml (0.368 mmol) diisopropylethylamine and 35 mg (0.263 mmol) of 1-phenyl-cyclopropylamine are added. The reaction mixture is stirred for 16 hours at ambient temperature and 24 hours at 40° C. 64.14 mg (0.344 mmol) piperazine and 0.064 ml (0.368 mmol) diisopropylethylamine are added, the mixture is stirred for 16 hours at 100° C. Then the reaction mixture is concentrated by evaporation, 15 ml of 50% trifluoroacetic acid in dichloromethane are added and the mixture is stirred for 3 hours at ambient temperature. The reaction mixture is concentrated by evaporation, the residue is extracted with dichloromethane and 1 N sodium hydroxide solution. The combined organic phases are dried and evaporated to dryness. The residue is purified by chromatography. Yield: 21 mg (=18% of theoretical)

Compound 13: a) 1-(3,4-dimethoxy-phenyl)-ethylamine: 37.00 ml (111 mmol) methylmagnesium bromide in diethyl ether are taken, a solution of 6.00 g (36.40 mmol) 3,4-dimethoxy-benzonitrile in 50 ml of tetrahydrofuran is added dropwise while cooling with ice, then the mixture is stirred for 3 hours while cooling continues. After the addition of 0.82 eq methylmagnesium bromide solution the mixture is stirred for 1.5 hours. Then 120 ml of methanol are added dropwise, then 2.78 g (72.80 mmol) sodium borohydride are added batchwise. The reaction mixture is stirred for 16 hours at ambient temperature, then concentrated in vacuo, and combined with water and chloroform. The mixture is adjusted to pH 1, the phases are separated. The aqueous phase is extracted with chloroform, then made alkaline and extracted again with chloroform. The organic phase is dried and evaporated to dryness. Yield: 1.71 g (=26% of theoretical)

b) (6-chloro-2-piperazin-1-yl-4-pyrrolidin-1-yl-pteridin-7-yl)-[1-(3,4-dimethoxy-phenyl)-ethyl]-amine (Example 13): 80 mg (0.263 mmol) 2,6,7-trichloro-4-pyrrolidin-1-yl-pteridine are dissolved in 5 ml dioxane, and 0.064 ml (0.368 mmol) diisopropylethylamine and 48 mg (0.265 mmol) 1-(3,4-dimethoxy-phenyl)-ethylamine are added. The reaction mixture is stirred for 72 hours at 40° C. 113 mg (1.31 mmol) piperazine are dissolved in 10 ml dioxane, heated to 80° C. and the reaction mixture is added dropwise. It is stirred for 2 hours, then the reaction mixture is added dropwise to 20 ml ice water and extracted with dichloromethane. The organic phase is dried and evaporated to dryness. The residue is purified by chromatography, the corresponding fraction is concentrated by evaporation.

Yield: 73 mg (=56% of theoretical)

Compound 14: a) C-cyclopropyl-C-phenyl-methylamine: 60.00 ml (30 mmol) cyclopropylmagnesium bromide in tetrahydrofuran are taken, a solution of 1.10 ml (10.22 mmol) benzonitrile in 15 ml of tetrahydrofuran is added dropwise while cooling with an ice bath. The mixture is stirred for 5.5 hours with further cooling. Then 30 ml of methanol are added dropwise and 800 mg (20.94 mmol) sodium borohydride are added batchwise. The reaction mixture is stirred for 16 hours at ambient temperature, then concentrated by evaporation. The residue is combined with chloroform and water, adjusted to pH 1 and the phases are separated. The aqueous phase is extracted with chloroform, then made alkaline and again extracted with chloroform. The resulting organic phase is dried and evaporated to dryness. Yield: 1.38 g (=92% of theoretical)

b) C-(6-chloro-2-piperazin-1-yl-4-pyrrolidin-1-yl-pteridin-7-yl)-C-cyclopropyl-C-phenyl-methylamine (Example 14): 80 mg (0.263 mmol) 2,6,7-trichloro-4-pyrrolidin-1-yl-pteridine are dissolved in 5 ml dioxane, and 0.064 ml (0.368 mmol) diisopropylethylamine and 38.67 mg (0.263 mmol) 1-phenyl-cyclopropylamine are added. The reaction mixture is stirred for 72 hours at ambient temperature. 113 mg (1.31 mmol) piperazine are dissolved in 10 ml dioxane, heated to 80° C. and the reaction mixture is added dropwise. The resulting mixture is stirred for 2 hours, then added dropwise to 20 ml ice water and extracted with dichloromethane. The organic phase is dried and evaporated to dryness. The residue is purified by chromatography, the corresponding fraction is concentrated by evaporation and triturated with diethyl ether/petroleum ether.

Yield: 47.70 mg (=39% of theoretical)

Compound 15: a) 1-(4-chlorophenyl)-cyclopropylamine: 500 mg (2.54 mmol) 1-(4-chlorophenyl)-cyclopropane-carboxylic acid, 1.20 ml (5.38 mmol) phosphoric acid diphenylesterazide and 0.39 ml (2.80 mmol) triethylamine are placed in 10 ml of dimethylformamide, then stirred for 16 hours at ambient temperature. Then the reaction mixture is added dropwise at 100° C. within 2 hours to 50 ml of water and 10 ml of 1 N hydrochloric acid, cooled and neutralised with sodium hydroxide solution. The precipitate formed is suction filtered, the filtrate is extracted with ethyl acetate. The organic phase is dried and evaporated to dryness. The residue is extracted acidically, the aqueous phase is neutralised and extracted with dichloromethane. The resulting organic phase is dried and evaporated to dryness. Yield: 145 mg (=34% of theoretical)

b) [1-(4-chlorophenyl)-cyclopropyl]-(6-chloro-2-piperazin-1-yl-4-pyrrolidin-1-yl-pteridin-7-yl)-amine (Example 15): 80 mg (0.263 mmol) 2,6,7-trichloro-4-pyrrolidin-1-yl-pteridine are dissolved in 5 ml dioxane, 0.064 ml (0.368 mmol) diisopropylethylamine and 44 mg (0.263 mmol) 1-(4-chlorophenyl)-cyclopropylamine added, then the mixture is heated to 40° C. The reaction mixture is stirred for 24 hours, another 1 equivalent of 1-(4-chlorophenyl)-cyclopropylamine is added and the mixture is stirred for a further 24 hours at 40° C. Then the reaction mixture is filtered through silica gel and concentrated by evaporation. 113 mg (1.31 mmol) piperazine are dissolved in 15 ml dioxane, heated to 80° C. and the reaction mixture is added dropwise. It is stirred for 1 hour, then the reaction mixture is added dropwise to 20 ml ice water and extracted with dichloromethane. The organic phase is dried and evaporated to dryness. The residue is purified by chromatography, the corresponding fraction is concentrated by evaporation and triturated with petroleum ether/diethyl ether.

Yield: 108 mg (=85% of theoretical)

Compound 16: a) 1-(3-bromophenyl)-cyclopropylamine: 500 mg (2.07 mmol) 1-(3-bromophenyl)-cyclopropane-carboxylic acid, 0.46 ml (2.07 mmol) phosphoric acid diphenylesterazide and 0.32 ml (2.28 mmol) triethylamine are placed in 10 ml of dimethylformamide, then stirred for 16 hours at ambient temperature. Then the reaction mixture is added dropwise at 100° C. within 2 hours to 50 ml of water and 10 ml 1 N hydrochloric acid, cooled and neutralised with sodium hydroxide solution. The precipitate formed is suction filtered, the filtrate is extracted with ethyl acetate. The organic phase is dried and evaporated to dryness. Yield: 332 mg (=75% of theoretical)

b) [1-(3-bromophenyl)-cyclopropyl]-(6-chloro-2-piperazin-1-yl-4-pyrrolidin-1-yl-pteridin-7-yl)-amine (Example 16): 80 mg (0.263 mmol) 2,6,7-trichloro-4-pyrrolidin-1-yl-pteridine are dissolved in 5 ml dioxane, 0.064 ml (0.368 mmol) diisopropylethylamine and 56 mg (0.263 mmol) 1-(3-bromophenyl)-cyclopropylamine are added, then the mixture is heated to 40° C. The reaction mixture is stirred for 72 hours. 113 mg (1.31 mmol) piperazine are dissolved in 15 ml dioxane, heated to 80° C. and the reaction mixture is added dropwise. It is stirred for 1 hour, then the reaction mixture is added dropwise to 20 ml ice water and extracted with dichloromethane. The organic phase is dried and evaporated to dryness. The residue is purified by chromatography, the corresponding fraction is concentrated by evaporation and triturated with petroleum ether/diethyl ether.

Yield: 125 mg (=90% of theoretical)

Compound 17: a) 1-p-tolyl-cyclopropylamine: 500 mg (2.84 mmol) 1-p-tolyl-cyclopropane-carboxylic acid, 0.63 ml (2.84 mmol) phosphoric acid diphenylesterazide and 0.40 ml (2.84 mmol) triethylamine are placed in 10 ml of dimethylformamide, then stirred for 16 hours at ambient temperature. Then the reaction mixture is added dropwise at 100° C. within 2 hours to 50 ml of water and 10 ml 1 N hydrochloric acid, cooled and neutralised with sodium hydroxide solution. The precipitate formed is suction filtered, the filtrate is extracted with ethyl acetate. The organic phase is dried and evaporated to dryness. The residue is extracted acidically, the aqueous phase is neutralised and extracted with dichloromethane. The resulting organic phase is dried and evaporated to dryness. Yield: 110 mg (=26% of theoretical)

b) (6-chloro-2-piperazin-1-yl-4-pyrrolidin-1-yl-pteridin-7-yl)-(1p-tolyl-cyclopropyl)-amine (Example 17): 80 mg (0.263 mmol) 2,6,7-trichloro-4-pyrrolidin-1-yl-pteridine are dissolved in 5 ml dioxane, and 0.064 ml (0.368 mmol) diisopropylethylamine and 43 mg (0.292 mmol) 1-p-tolyl-cyclopropylamine are added, then the mixture is heated to 40° C. The reaction mixture is stirred for 72 hours. 113 mg (1.31 mmol) piperazine are dissolved in 15 ml dioxane, heated to 80° C. and the reaction mixture is added dropwise. It is stirred for 1 hour, then the reaction mixture is added dropwise to 20 ml of ice water and extracted with dichloromethane. The organic phase is dried and evaporated to dryness. The residue is purified by chromatography, the corresponding fraction is concentrated by evaporation and triturated with petroleum ether/diethyl ether. Yield: 80 mg (=65% of theoretical)

Compound 20: a) methyl (S)-phenyl-(2,2,2-trifluoro-acetylamino)-acetate: 3.00 g (14.877 mmol) (S)-phenylglycinemethylester hydrochloride and 2.48 ml (17.853 mmol) triethylamine are placed in 25 ml of tetrahydrofuran and cooled to −78° C. 2.50 ml (18 mmol) trifluoroacetic anhydride are slowly added dropwise. After removal of the cooling the reaction mixture is stirred for 16 hours at ambient temperature. Then it is combined with water, then extracted with ethyl acetate. The combined organic phases are washed, dried and evaporated to dryness. Yield: 3.90 g (=100% of theoretical)

b) (S)-2,2,2-trifluoro-N-(2-hydroxy-2-methyl-1-phenyl-propyl)-acetamide: 1.00 g (3.829 mmol) methyl (S)-phenyl-(2,2,2-trifluoro-acetylamino)-acetate are placed in 40 ml diethyl ether, 3.83 ml (11.486 mmol) methylmagnesium iodide solution are slowly added dropwise. The temperature should not exceed 20° C. The suspension is stirred for 16 hours at ambient temperature, then poured onto ice water. Ammonium chloride is added until the precipitate has dissolved. The aqueous phase is extracted with diethyl ether, the combined organic phases are dried and evaporated to dryness.

Yield: 1.20 g (>100% of theoretical)

c) (S)-1-amino-2-methyl-1-phenyl-propan-2-ol: 1.20 g (4.593 mmol) (S)-2,2,2-trifluoro-N-(2-hydroxy-2-methyl-1-phenyl-propyl)-acetamide and 0.515 g (9.187 mmol) potassium hydroxide are placed in 15 ml of methanol and stirred for 16 hours at 60° C. Then the reaction mixture is combined with water and extracted with dichloromethane. The organic phases are combined, dried and evaporated to dryness.

Yield: 500 mg (=53% of theoretical)

d) (S)-1-(6-chloro-2-piperazin-1-yl-4-pyrrolidin-1-yl-pteridin-7-ylamino)-2-methyl-1-phenyl-propan-2-ol (Example 20): 100 mg (0.279 mmol) (S)-2,6,7-trichloro-4-pyrrolidin-1-yl-pteridine are dissolved in 15 ml dioxane, 0.053 ml (0.307 mmol) diisopropylethylamine and 51.24 mg (0.279 mmol) 1-amino-2-methyl-1-phenyl-propan-2-ol are added, then the mixture is heated to 40° C. The reaction mixture is stirred for 16 hours. A further 0.4 eq of 1-amino-2-methyl-1-phenyl-propan-2-ol are added, and the mixture is stirred for 3 hours at 40° C. 120 mg (1.40 mmol) piperazine are dissolved in 5 ml dioxane, heated to 80° C. and the reaction mixture is added dropwise. It is stirred for 16 hours, then the reaction solution is concentrated in vacuo and added dropwise to 50 ml ice water. The precipitate formed is suction filtered and purified by chromatography. Corresponding fractions are combined, evaporated to dryness. The residue is taken up in dioxane and freeze-dried.

Yield: 45 mg (=33% of theoretical)

Compound 21: a) 3-(1-amino-ethyl)-benzonitrile: 9.40 g (64.757 mmol) 3-cyano-acetophenone, 40.00 g (518.941 mmol) ammonium acetate and 10.00 g (186.951 mmol) ammonium chloride are placed in methanol. The mixture is stirred for 16 hours at 40° C. 2.90 g (46.149 mmol) sodium cyanoborohydride are added, then the mixture is stirred for another 16 hours. The reaction mixture is adjusted to pH3 with glacial acetic acid, then the methanol is evaporated down. On cooling a precipitate settles out. This is suction filtered. The filtrate is made alkaline with conc. sodium hydroxide solution, the precipitate thus formed is suction filtered. The filtrate is extracted with diethyl ether, the combined organic phases are dried and evaporated to dryness. The residue is purified by vacuum distillation.

Yield: 1.10 g (=12% of theoretical)

b) 3-[1-(6-chloro-2-piperazin-1-yl-4-pyrrolidin-1-yl-pteridin-7-ylamino)-ethyl]-benzonitrile (Example 21): 90.00 mg (0.296 mmol) 2,6,7-trichloro-4-pyrrolidin-1-yl-pteridine and 0.057 ml (0.304 mmol) diisopropylethylamine are dissolved in 10 ml dioxane, a solution of 43.20 mg (0.296 mmol) 3-(1-amino-ethyl)-benzonitrile in 5 ml dioxane at ambient temperature is added dropwise. The reaction mixture is stirred for 2 hours at ambient temperature and for 16 hours at 40° C., while another 1 eq diisopropylethylamine and 3-(1-amino-ethyl)-benzonitrile are added. 127 mg (1.47 mmol) piperazine are dissolved in 20 ml dioxane, the mixture is heated to 80° C. and the reaction mixture is added dropwise. It is stirred for 16 hours, then the reaction solution is concentrated in vacuo and added dropwise to 50 ml ice water. The precipitate formed is suction filtered and purified by chromatography. Corresponding fractions are combined, evaporated to dryness. The residue is taken up in dioxane and freeze-dried. Yield: 30.0 mg (=22% of theoretical)

Compound 24: a) 1-(3,4-dimethoxy-benzyl)-cyclopropylamine: 5.20 g (28.76 mmol) 3,4-dimethoxybenzylcyanide are placed in 150 ml diethyl ether and 9.00 ml (30.708 mmol) titanium(IV) isopropoxide are added. While cooling with ice 20.00 ml (60 mmol) 3 molar ethylmagnesium bromide solution are added dropwise, then the mixture is stirred for 0.5 hours. Then 7.60 ml (59.97 mmol) boron trifluoride etherate are added dropwise and the mixture is stirred for 0.5 hours. Then while being cooled the reaction mixture is combined with 90 ml 1 N sodium hydroxide solution and stirred for 1 hour at ambient temperature. The organic phase is separated off, the aqueous phase is extracted with diethyl ether. The combined organic phases are washed with saturated sodium sulphonate solution and extracted acidically. The resulting aqueous phase is extracted with dichloromethane, the organic extracts are dried and evaporated to dryness. The residue is purified by chromatography. Yield: 1.60 g (=27% of theoretical)

b) (6-chloro-2-piperazin-1-yl-4-pyrrolidin-1-yl-pteridin-7-yl)-[1-(3,4-dimethoxybenzyl)-cyclopropyl]-amine (Example 24): 80 mg (0.263 mmol) 2,6,7-trichloro-4-pyrrolidin-1-yl-pteridine are suspended in 5 ml dioxane, and 54 mg (0.260 mmol) 1-(3,4-dimethoxybenzyl)-cyclopropylamine and 0.064 ml (0.368 mmol) diisopropylethylamine are added. The mixture is stirred for 72 hours at 40° C. 113 mg (1.31 mmol) piperazine are dissolved in 15 ml dioxane, heated to 80° C. and the reaction mixture is added dropwise. It is stirred for 2 hours, then added dropwise to 20 ml of ice water. It is extracted with dichloromethane, the organic phase is dried and evaporated to dryness. The residue is purified by chromatography. Corresponding fraction is evaporated to dryness, then triturated with petroleum ether/diethyl ether. Yield: 78 mg (=57% of theoretical)

Compound 27: a) 1-(4-fluorophenyl)-cyclopropylamine: 5.00 g (41.28 mmol) 4-fluorobenzonitrile and 12.10 g (41.28 mmol) titanium(IV) isopropoxide are placed in 100 ml diethyl ether and cooled to 70° C. 30.28 ml (90.83 mmol) 3 molar ethylmagnesium bromide solution are added dropwise, then the mixture is stirred for 0.1 hours. After heating to ambient temperature 10.42 ml (82.56 mmol) boron trifluoride etherate are added dropwise and the mixture is stirred for 1 hour. Then the reaction mixture is combined with 56 ml 1 N hydrochloric acid, then 80 ml 4 N sodium hydroxide solution are added. The precipitate formed is suction filtered and discarded. The filtrate is extracted with water, the organic phases are combined, dried and evaporated to dryness. The residue is taken up in dichloromethane, extracted acidically and neutralised. The organic phase is dried and evaporated to dryness. The residue is purified by chromatography. Yield: 1.818 g (=29% of theoretical)

b) (6-chloro-2-piperazin-1-yl-4-pyrrolidin-1-yl-pteridin-7-yl)-[1-(4-fluorophenyl)-cyclopropyl]-amine (Example 27): 80 mg (0.263 mmol) 2,6,7-trichloro-4-pyrrolidin-1-yl-pteridine are suspended in 5 ml dioxane, 40 mg (0.264 mmol) 1-(4-isopropyl-phenyl)-cyclopropylamine and 0.064 ml (0.368 mmol) diisopropylethylamine are added. The mixture is stirred for 16 hours at 40° C. 113 mg (1.31 mmol) piperazine are dissolved in 15 ml dioxane, heated to 80° C. and the reaction mixture is added dropwise. It is stirred for 2 hours, then added dropwise to 20 ml of ice water. It is extracted with dichloromethane, the organic phase is dried and evaporated to dryness. The residue is purified by chromatography. Corresponding fraction is evaporated to dryness, then triturated with petroleum ether/diethyl ether. Yield: 52 mg (=42% of theoretical)

Compound 29: a) 1-(4-isopropyl-phenyl)-cyclopropylamine: 2.00 g (14 mmol) 4-isopropylbenzonitrile and 4.04 g (13.77 mmol) titanium(IV) isopropoxide are placed in 60 ml diethyl ether and cooled to 70° C. 10.10 ml (30.30 mmol) 3 molar ethylmagnesium bromide solution are added dropwise, then the mixture is stirred for 0.1 hours. After heating to ambient temperature 3.48 ml (27.55 mmol) boron trifluoride etherate are added dropwise and the mixture is stirred for 1 hour. Then the reaction mixture is combined with 25 ml 1 N hydrochloric acid, then 32 ml 4 N sodium hydroxide solution are added. The precipitate thus formed is suction filtered and discarded. The filtrate is extracted with water, the organic phases are combined, dried and evaporated to dryness. The residue is taken up in dichloromethane, extracted acidically and neutralised. The organic phase is dried and evaporated to dryness. The residue is purified by chromatography.

Yield: 425 mg (=18% of theoretical)

b) (6-chloro-2-piperazin-1-yl-4-pyrrolidin-1-yl-pteridin-7-yl)-[1-(4-isopropyl-phenyl)-cyclopropyl]-amine (Example 29): 80 mg (0.263 mmol) 2,6,7-trichloro-4-pyrrolidin-1-yl-pteridine are suspended in 5 ml dioxane, 51.0 mg (0.290 mmol) 1-(4-isopropyl-phenyl)-cyclopropylamine and 0.064 ml (0.368 mmol) diisopropylethylamine are added. The mixture is stirred for 72 hours at 40° C. 113 mg (1.31 mmol) piperazine are dissolved in 15 ml dioxane, heated to 80° C. and the reaction mixture is added dropwise. It is stirred for 2 hours, then added dropwise to ice water. It is extracted with dichloromethane, the organic phase is dried and evaporated to dryness. The residue is purified by chromatography. Corresponding fraction is evaporated to dryness, then triturated with petroleum ether/diethyl ether. Yield: 77.50 mg (=60% of theoretical)

Compound 31: a) methyl (S)-amino-(4-fluorophenyl)-acetate: 500 mg (2.96 mmol) (S)-4-fluorophenylglycine are suspended in 10 ml of methanol, and while cooling with ice 0.43 ml (5.91 mmol) thionyl chloride are carefully added dropwise. The mixture is stirred for 16 hours at ambient temperature, then evaporated to dryness. Yield: 700 mg b) methyl (4-fluorophenyl)-(2,2,2-trifluoroacetylamino)-acetate: 700 mg (3.19 mmol) methyl (S)-amino-(4-fluorophenyl)-acetate are suspended in 5 ml of tetrahydrofuran, 0.53 ml (40 mmol) triethylamine are added. The mixture is cooled to −70° C., then 0.54 ml (40 mmol) trifluoroacetic anhydride are added dropwise. After removal of the cooling the reaction mixture is stirred for 16 hours at ambient temperature. Then water and potassium hydrogen carbonate are added and the mixture is extracted with ethyl acetate. The combined organic phases are washed, dried and evaporated to dryness.

Yield: 680 mg (=76% of theoretical)

c) (S)-2,2,2-trifluoro-N-[1-(4-fluorophenyl)-2-hydroxy-2-methyl-propyl]-acetamide: 680 mg (2.44 mmol) methyl (S)-(4-fluorophenyl)-(2,2,2-trifluoroacetylamino)-acetate are placed in 20 ml of tetrahydrofuran, then 4.06 ml (12.18 mmol) methylmagnesium iodide solution are slowly added dropwise. The temperature should not exceed 20° C. The reaction mixture with insoluble precipitate is stirred for 16 hours at ambient temperature, then poured onto ice water. Ammonium chloride is added until the precipitate is dissolved. The aqueous phase is extracted with diethyl ether, the combined organic phases are dried and evaporated to dryness. Yield: 570 mg (=84% of theoretical)

d) (S)-1-amino-1-(4-fluorophenyl)-2-methyl-propan-2-ol: 570 mg (2.04 mmol) (S)-2,2,2-trifluoro-N-[1-(4-fluorophenyl)-2-hydroxy-2-methyl-propyl]-acetamide and 221 mg (40 mmol) potassium hydroxide are placed in 7 ml of methanol and stirred for 16 hours at 60° C. Then the reaction mixture is combined with water and extracted with dichloromethane. The organic phases are combined, dried and evaporated to dryness.

Yield: 300 mg (=80% of theoretical)

e) 1-(6-chloro-2-piperazin-1-yl-4-pyrrolidin-1-yl-pteridin-7-ylamino)-(S)-1-(4-fluorophenyl)-2-methyl-propan-2-ol (Example 31): 100 mg (0.279 mmol) (S)-2,6,7-trichloro-4-pyrrolidin-1-yl-pteridine are dissolved in 5 ml dioxane, 0.053 ml (0.307 mmol) diisopropylethylamine and 66.20 mg (0.360 mmol) 1-amino-1-(4-fluorophenyl)-2-methyl-propan-2-ol are added, then the mixture is heated to 40° C. The reaction mixture is stirred for 16 hours. 120 mg (1.40 mmol) piperazine are dissolved in 5 ml dioxane, heated to 80° C. and the reaction mixture is added dropwise. It is stirred for 16 hours, then the reaction solution is concentrated in vacuo and added dropwise to ice water. The precipitate formed is suction filtered and purified by chromatography. Corresponding fractions are combined, evaporated to dryness. The residue is taken up in dioxane and freeze-dried.

Yield: 75 mg (=54% of theoretical)

Compound 34: a) benzaldehyde tosyl hydrazone: 5.00 g (26.85 mmol) p-toluene-sulphonylhydrazide are placed in 10 ml of methanol, 2.37 ml (23.30 mmol) benzaldehyde are slowly added dropwise. A precipitate settles out. This is suction filtered and washed with methanol. Then the precipitate is recrystallised from methanol.

Yield: 3.14 g (43% of theoretical)

b) Racemic-cis-2-(2-phenyl-cyclopropyl)-isoindole-1,3-dione: 2.00 g (7.29 mmol) benzaldehyde tosyl hydrazone are placed in 40 ml of tetrahydrofuran and cooled to −70° C. 7.29 ml (7.29 mmol) LiHMDS lithium bis(trimethylsilyl)amide (1 M solution in tetrahydrofuran) are added, then the mixture is stirred for 0.25 hours at −78° C. The reaction mixture is slowly heated to ambient temperature, then concentrated by evaporation. The residue is dissolved in 50 ml dioxane, combined with 0.166 g (1 mmol) benzyltriethylammonium chloride and 0.032 g rhodium acetate-dimer, and 6.31 g (36.45 mmol) 2-vinyl-isoindole-1,3-dione added. The reaction mixture is stirred for 80 hours, then extracted with water and dichloromethane. The organic phase is dried and evaporated to dryness. The residue is purified by chromatography.

Yield: 0.650 g (34% of theoretical)

c) Racemic-cis-2-phenyl-cyclopropylamine: 0.460 g (1.75 mmol) 2-(2-phenyl-cyclopropyl)-isoindole-1,3-dione (chiral) are placed in 6 ml of ethanol, 0.115 g (1.83 mmol) hydrazine hydrate dissolved in 12 ml of ethanol are added. The reaction mixture is stirred for 15 hours at 40° C. Then 0.58 ml 1 N hydrochloric acid are added and the mixture is then stirred for 3 hours. After cooling the precipitate formed is suction filtered and washed with ethanol. The filtrate is concentrated by evaporation, the residue is taken up in 12 ml 1 N hydrochloric acid and extracted with diethyl ether. The aqueous phase is made basic and extracted with dichloromethane. The organic phase is dried and evaporated to dryness.

Yield: 0.090 g (39% of theoretical)

Compound 35: a) Racemic 2-phenyl-cyclopropyl cis-acetate: 10.00 g (36.45 mmol) benzaldehyde tosyl hydrazone are placed in 200 ml of tetrahydrofuran and cooled to −70° C.

36.45 ml (36.45 mmol) LiHMDS lithium bis(trimethylsilyl) amide (1 molar solution in tetrahydrofuran) are added, then the mixture is stirred for 0.25 hours at −78° C. The reaction mixture is slowly heated to ambient temperature, then evaporated down in vacuo. The residue is dissolved in 250 ml dioxane, combined with 0.830 g (4 mmol) benzyltriethylammonium chloride and 0.161 g rhodium acetate dimer, and 33.59 ml (36.45 mmol) vinyl acetate are added. The reaction mixture is stirred for 70 hours, then extracted with water and dichloromethane. The organic phase is washed with conc. sodium chloride solution, dried and evaporated to dryness. The residue is purified by chromatography. Yield: 0.800 g (11% of theoretical)

b) Racemic-cis-2-phenyl-cyclopropanol: 0.280 g (1.59 mmol) 2-phenyl-cyclopropyl acetate (chiral) are dissolved under argon in 1.50 ml diethyl ether, and 2.00 ml (3.20 mmol) methyl lithium dissolved in 2 ml diethyl ether are added dropwise within 0.25 hours. The reaction mixture is stirred for 0.5 hours at ambient temperature, then added to 6 ml of conc. boric acid. The mixture is diluted with water and extracted. The organic phase is washed with saturated sodium chloride solution, dried and evaporated to dryness.

Yield: 0.200 g (94% of theoretical)

The following are a number of compounds, mentioned by way of example, which may be prepared by one of the methods of synthesis outlined above.

| # | $R^1$ | $R^2$ | $R^3$ | M + H |
|---|---|---|---|---|
| 1. | pyrrolidin-1-yl | piperazin-1-yl | (R)-1-phenylethylamino | 439/441 |
| 2. | pyrrolidin-1-yl | piperazin-1-yl | (S)-1-phenylethylamino | 439/441 |
| 3. | pyrrolidin-1-yl | piperazin-1-yl | (R)-2-hydroxy-1-phenylethylamino | 455/457 |
| 4. | pyrrolidin-1-yl | piperazin-1-yl | (S)-2-hydroxy-1-phenylethylamino | 455/457 |
| 5. | pyrrolidin-1-yl | piperazin-1-yl | (R)-methyl phenylglycinate | 483/485 |
| 6. | pyrrolidin-1-yl | piperazin-1-yl | (S)-methyl phenylglycinate | 483/485 |

-continued

| # | R¹ | R² | R³ | M + H |
|---|---|---|---|---|
| 7. | pyrrolidin-1-yl | piperazin-1-yl | (S)-NH-CH(Ph)-C(O)NH₂ | 468/470 |
| 8. | pyrrolidin-1-yl | piperazin-1-yl | (R)-NH-CH(Ph)-C(O)NH₂ | 468/470 |
| 9. | pyrrolidin-1-yl | piperazin-1-yl | NH-CH(CH₃)-Ph | 439/441 |
| 10. | pyrrolidin-1-yl | piperazin-1-yl | (S)-NH-CH(Ph)-COOH | 469/471 |
| 11. | pyrrolidin-1-yl | piperazin-1-yl | (R)-NH-CH(Ph)-COOH | 469/471 |
| 12. | pyrrolidin-1-yl | piperazin-1-yl | NH-C(cyclopropyl)(Ph) | 451/453 |
| 13. | pyrrolidin-1-yl | piperazin-1-yl | NH-CH(CH₃)-(3,4-dimethoxyphenyl) | 499/450 |
| 14. | pyrrolidin-1-yl | piperazin-1-yl | NH-CH(cyclopropyl)(Ph) | 465/467 |

-continued

| # | R¹ | R² | R³ | M + H |
|---|---|---|---|---|
| 15. | *—N(pyrrolidine) | *—N(piperazine)NH | *—NH—C(cyclopropyl)(4-chlorophenyl) | 485/487/489 |
| 16. | *—N(pyrrolidine) | *—N(piperazine)NH | *—NH—C(cyclopropyl)(3-bromophenyl) | 529/531/533 |
| 17. | *—N(pyrrolidine) | *—N(piperazine)NH | *—NH—C(cyclopropyl)(4-methylphenyl) | 465/467 |
| 18. | *—N(pyrrolidine) | *—N(piperazine)NH | *—NH—C(CH₃)₂-phenyl | 453/455 |
| 19. | *—N(pyrrolidine) | *—N(piperazine)NH | *—NH—CH(phenyl)-C(CH₃)₂OH | 483/485 |
| 20. | *—N(pyrrolidine) | *—N(piperazine)NH | *—NH—CH(phenyl)-C(CH₃)₂OH | 483/485 |
| 21. | *—N(pyrrolidine) | *—N(piperazine)NH | *—NH—CH(CH₃)-(3-cyanophenyl) | 464/466 |
| 22. | *—N(pyrrolidine) | *—N(piperazine)NH | *—NH—CH₂—CH(CH₃)-(3,4-dimethoxyphenyl) | 513/515 |

-continued

| # | R¹ | R² | R³ | M + H |
|---|----|----|----|-------|
| 23. | *—N(pyrrolidine) | *—N(piperazine)NH | *—NH—CH(CH₂-)—C(OMe)H, 3,4-dimethoxyphenyl with OMe on carbon | 529/531 |
| 24. | *—N(pyrrolidine) | *—N(piperazine)NH | *—NH—C(cyclopropyl)(CH₂-3,4-dimethoxyphenyl) | 525/527 |
| 25. | *—N(pyrrolidine) | *—N(piperazine)NH | *—NH—CH₂—CH(OH)—phenyl | 455/457 |
| 26. | *—N(pyrrolidine) | *—N(piperazine)NH | *—NH—CH(4-F-phenyl)—CH₂OH | 473/475 |
| 27. | *—N(pyrrolidine) | *—N(piperazine)NH | *—NH—C(cyclopropyl)(4-F-phenyl) | 469/471 |
| 28. | *—N(pyrrolidine) | *—N(piperazine)NH | *—NH—CH(4-F-phenyl)—CH₂OH | 473/475 |
| 29. | *—N(pyrrolidine) | *—N(piperazine)NH | *—NH—C(cyclopropyl)(4-iPr-phenyl) | 493/495 |

-continued

| # | R¹ | R² | R³ | M + H |
|---|---|---|---|---|
| 30. | *-pyrrolidin-1-yl | *-piperazin-1-yl (NH) | *-NH-CH(4-F-C₆H₄)-C(CH₃)₂-OH (one enantiomer) | 501/503 |
| 31. | *-pyrrolidin-1-yl | *-piperazin-1-yl (NH) | *-NH-CH(4-F-C₆H₄)-C(CH₃)₂-OH (other enantiomer) | 501/503 |
| 32. | *-pyrrolidin-1-yl | *-piperazin-1-yl (NH) | *-NH-CH(4-F-C₆H₄)-CH₂-CH₂-OH | 687/689 |
| 33. | *-pyrrolidin-1-yl | *-piperazin-1-yl (NH) | *-NH-(2-phenylcyclopropyl) | 451/453 |
| 34. | *-pyrrolidin-1-yl | *-piperazin-1-yl (NH) | *-NH-(trans-2-phenylcyclopropyl) | 451/453 |
| 35. | *-pyrrolidin-1-yl | *-piperazin-1-yl (NH) | *-NH-(trans-2-phenylcyclopropyl, opposite enantiomer) | 451/453 |

-continued

| # | R¹ | R² | R³ | M + H |
|---|----|----|----|-------|
| 36. | *—N(pyrrolidine) | *—N(piperazine)NH | *—NH-(cyclopropyl)-phenyl | 451/453 |
| 37. | *—N(pyrrolidine) | *—N(piperazine)NH | *—NH-(cyclopropyl)-phenyl | 451/453 |
| 38. | *—N(pyrrolidine) | *—N(piperazine)NH | *—O-(cyclopropyl)-phenyl | 451/453 |
| 39. | *—N(pyrrolidine) | *—N(piperazine)NH | *—O-(cyclopropyl)-phenyl | 451/453 |
| 40. | *—N(pyrrolidine) | *—N(piperazine)NH | *—O-(cyclopropyl)-phenyl | 451/453 |
| 41. | *—N(pyrrolidine) | *—N(piperazine)NH | *—O-(cyclopropyl)-phenyl | 451/453 |

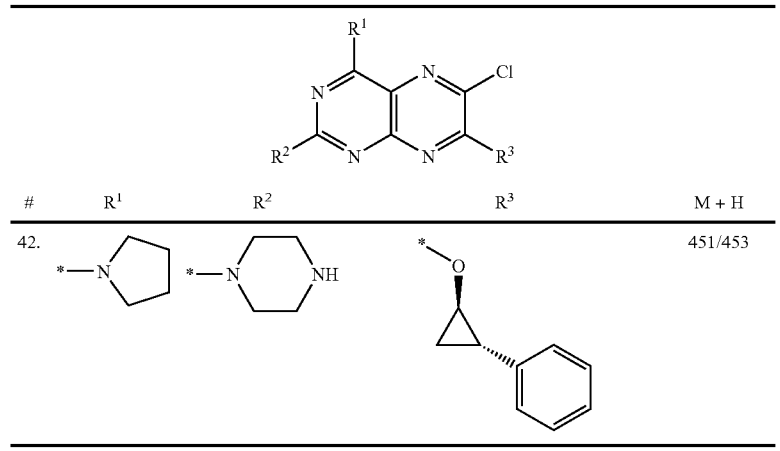

INDICATIONS

As has been found, the compounds of formula 1 are characterised by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis or interstitial pneumonia or pulmonary fibrosis of various causes, such as, for example, as a result of aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides interstinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

An outstanding aspect of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

COMBINATIONS

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, dopamine agonists, H1-antihistamines, PAF-antagonists and PI3-kinase inhibitors or double or triple combinations thereof, such as for example combinations of

- betamimetics with corticosteroids, PDE4-inhibitors, EGFR-inhibitors or LTD4-antagonists,
- anticholinergics with betamimetics, corticosteroids, PDE4-inhibitors, EGFR-inhibitors or LTD4-antagonists,
- corticosteroids with PDE4-inhibitors, EGFR-inhibitors or LTD4-antagonists
- PDE4-inhibitors with EGFR-inhibitors or LTD4-antagonists
- EGFR-inhibitors with LTD4-antagonists.

The invention also encompasses combinations of three active substances, each selected from one of the above-mentioned categories of compounds.

FORMULATIONS

In another aspect the invention relates to medicaments for the treatment of respiratory complaints, which contain one or more of the above-mentioned pteridines of formula 1, which are used in combination with one or more additional active substances selected from among the betamimetics, anticholinergics, corticosteroids, PI3-kinase inhibitors, LTD4-antagonists, EGFR-inhibitors, dopamine agonists, H1-antihistamines or PAF-antagonists, preferably betamimetics, anticholinergics or corticosteroids, together or successively, for simultaneous, sequential or separate administration.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable effect or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a pteridine and one or more combination partners selected from those described above.

What is claimed is:
1. A compound of the formula 1,

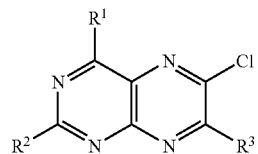

wherein
$R^1$ denotes pyrrolidin-1-yl;
$R^2$ denotes piperazin-1-yl;
$R^3$ denotes a group of formula 1a,

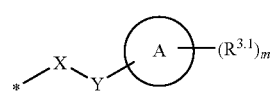

wherein
A denotes aryl;
X denotes $NR^{3.2}$;
Y denotes $C_{1-4}$-alkylene, substituted by one or more $R^{3.3}$;
m denotes 0, 1 or 2;
$R^{3.1}$ each independently of one another denote $C_{1-6}$-alkyl, aryl, $COOR^{3.1.1}$, $CONR^{3.1.1}R^{3.1.2}$, CN, $NR^{3.1.1}R^{3.1.2}$, $NHCOR^{3.1.1}$, $OR^{3.1.1}$, O—$C_{1-6}$-haloalkyl, $SO_2R^{3.1.1}$, $SO_2NH_2$, halogen, $C_{1-6}$-haloalkyl, $C_{1-6}$-alkyl-$CONH_2$, O—$C_{1-6}$-alkyl-$NH_2$, O—$C_{3-6}$-cycloalkyl, or O—$C_{1-4}$-alkylene-$C_{3-6}$-cycloalkyl;
$R^{3.1.1}$ denotes H or $C_{1-6}$-alkyl;
$R^{3.1.2}$ denotes H or $C_{1-6}$-alkyl; or
$R^{3.1}$ together with two atoms of A forms a 5- or 6-membered carbocyclic ring or a 5- or 6-membered heterocyclic ring which contains one or more oxygen or nitrogen atoms;
$R^{3.2}$ denotes H or $C_{1-6}$-alkyl;
$R^{3.3}$ each independently of one another denote $C_{1-6}$-alkyl, $C_{1-6}$-alkyl-OH, $C_{3-6}$-cycloalkyl, $C_{3-6}$-cycloalkyl-OH, O—$C_{1-6}$-alkyl; or $R^{3.3}$ together with one or two carbon atoms of Y forms a carbocyclic ring with 3, 4, 5 or 6 carbon atoms or a pharmacologically acceptable salt thereof.

2. A compound of formula 1, according to claim 1, wherein
$R^3$ is a group of the formula 1a, wherein
A denotes phenyl;
X denotes $NR^{3.2}$;
Y denotes $C_{1-4}$-alkylene, substituted by one or more $R^{3.3}$;
m denotes 0, 1 or 2;
$R^{3.1}$ each independently of one another denote $C_{1-4}$-alkyl, aryl, $COOR^{3.1.1}$, $CONR^{3.1.1}R^{3.1.2}$, CN, $NR^{3.1.1}R^{3.1.2}$, $NHCOR^{3.1.1}$, $OR^{3.1.1}$, $O-C_{1-4}$-haloalkyl, $SO_2R^{3.1.1}$, $SO_2NH_2$ or halogen;
wherein
$R^{3.1.1}$ denotes H or $C_{1-6}$-alkyl;
$R^{3.1.2}$ denotes H or $C_{1-6}$-alkyl;
$R^{3.2}$ denotes H or $C_{1-6}$-alkyl;
$R^{3.3}$ each independently of one another denote $C_{1-6}$-alkyl, $C_{1-6}$-alkyl-OH, $C_{3-6}$-cycloalkyl, $O-C_{1-6}$-alkyl; or
$R^{3.3}$ together with one or two carbon atoms of Y forms a carbocyclic ring with 3, 5 or 6 carbon atoms or a pharmacologically acceptable salt thereof.

3. A compound of the formula 1, according to claim 1, wherein
$R^3$ is a group of the formula 1a, wherein
A denotes phenyl;
X denotes $NR^{3.2}$;
Y denotes $C_{1-2}$-alkylene, substituted by one or more $R^{3.3}$;
m denotes 0, 1 or 2;
$R^{3.1}$ each independently of one another denote $C_{1-4}$-alkyl, aryl, COOH, COO—$C_{1-4}$-alkyl, $CONH_2$, CN, $NH_2$, NHCO—$C_{1-4}$-alkyl, OH, O—$C_{1-4}$-alkyl, O—$C_{1-4}$-haloalkyl, $SO_2$—$C_{1-4}$-alkyl, $SO_2NH_2$ or halogen;
$R^{3.2}$ denotes H or $C_{1-4}$-alkyl;
$R^{3.3}$ each independently of one another denote $C_{1-4}$-alkyl, $C_{1-4}$-alkyl-OH, $C_{3-6}$-cycloalkyl, O—$C_{1-4}$-alkyl; or
$R^{3.3}$ together with one or two carbon atoms of Y forms a carbocyclic ring with 3, 5 or 6 carbon atoms or a pharmacologically acceptable salt thereof.

4. A compound of the formula 1, according to claim 1, wherein
$R^3$ is a group of the formula 1a, wherein
A denotes phenyl;
X denotes $NR^{3.2}$;
Y denotes $C_{1-2}$-alkylene, substituted by one or more $R^{3.3}$;
m denotes 0, 1 or 2;
$R^{3.1}$ each independently of one another denote methyl, ethyl, propyl, Ph, COOH, COOMe, $CONH_2$, CN, $NH_2$, NHCOMe, OH, OMe, OEt, $OCF_3$, $OCHF_2$, $SO_2Me$, $SO_2NH_2$, F, Cl or Br;
$R^{3.2}$ denotes H or $C_{1-4}$-alkyl;
$R^{3.3}$ each independently of one another denote methyl, ethyl, propyl, butyl, $CH_2OH$, $CH_2CH_2OH$, $C(CH_2)_2OH$, cyclopropyl, OMe, OEt, OPr; or
$R^{3.3}$ together with one or two carbon atoms of Y forms a carbocyclic ring with 3, 5 or 6 carbon atoms or a pharmacologically acceptable salt thereof.

5. A compound of the formula 1, according to claim 1, wherein
$R^3$ is a group of the formula 1a, wherein
A denotes phenyl;
X denotes $NR^{3.2}$;
Y denotes $C_{1-2}$-alkylene, substituted by one or more $R^{3.3}$;
m denotes 0, 1 or 2;
$R^{3.1}$ each independently of one another denote methyl, iso-propyl, OMe, F, Cl, Br or CN,
$R^{3.2}$ denotes H;
$R^{3.3}$ each independently of one another denote methyl, cyclopropyl, $CH_2OH$, $CH_2CH_2OH$, $C(CH_2)_2OH$, OMe, or
$R^{3.3}$ together with one or two carbon atoms of Y forms a carbocyclic ring with 3 carbon atoms or a pharmacologically acceptable salt thereof.

6. A pharmaceutical composition comprising a compound of the formula 1, in accordance with claim 1, and a pharmaceutically acceptable carrier.

* * * * *